United States Patent
Moehring et al.

(10) Patent No.: US 6,635,017 B1
(45) Date of Patent: Oct. 21, 2003

(54) METHOD AND APPARATUS COMBINING DIAGNOSTIC ULTRASOUND WITH THERAPEUTIC ULTRASOUND TO ENHANCE THROMBOLYSIS

(75) Inventors: Mark A. Moehring, Seattle, WA (US); Arne H. Voie, Seattle, WA (US); Merrill P. Spencer, Seattle, WA (US)

(73) Assignee: Spentech, Inc., Seattle, WA (US)

( * ) Notice: Subject to any disclaimer, the term of this patent is extended or adjusted under 35 U.S.C. 154(b) by 0 days.

(21) Appl. No.: 09/500,708

(22) Filed: Feb. 9, 2000

(51) Int. Cl.[7] ............................... A61B 8/06; A61N 7/00
(52) U.S. Cl. ................ 600/439; 600/441; 600/454; 600/459; 601/2; 604/22
(58) Field of Search ........................ 600/439, 459, 600/454, 441; 601/2; 604/21, 22

(56) References Cited

U.S. PATENT DOCUMENTS

| | | | |
|---|---|---|---|
| 4,622,978 A | * | 11/1986 | Matsuo et al. ............... 600/441 |
| 4,757,820 A | | 7/1988 | Itoh |
| 5,307,816 A | * | 5/1994 | Hashimoto et al. ......... 600/439 |
| 5,509,413 A | * | 4/1996 | Akama et al. ............... 600/438 |
| 5,509,896 A | * | 4/1996 | Carter ............................ 601/2 |
| 5,558,092 A | * | 9/1996 | Unger et al. ................. 600/439 |
| 5,720,287 A | * | 2/1998 | Chapelon et al. ........... 600/439 |
| 5,961,456 A | * | 10/1999 | Gildenberg ................. 600/426 |
| 6,196,972 B1 | | 3/2001 | Moehring ................... 600/454 |

* cited by examiner

Primary Examiner—Ruth S. Smith
(74) Attorney, Agent, or Firm—Dorsey & Whitney LLP

(57) ABSTRACT

A method and apparatus for combining therapeutic pulsed or continuous-wave ultrasound with diagnostic pulsed ultrasound are described. In both a therapeutic mode and in a diagnostic mode, the ultrasound is administered from a single probe to a patient suffering from thrombosis. The ultrasound can have the same or different frequency ranges in the diagnostic and therapeutic modes. The pulsed or continuous-wave ultrasound in the therapeutic mode enhances a lysing effect of a thrombolytic agent. The pulsed ultrasound in the diagnostic mode allows monitoring of blood flow to locate a thrombus, to determine an optimal window to administer the therapeutic pulsed ultrasound, and to detect when recanalization has occurred. If an operator attends the device, a graphical display operates during the diagnostic mode to display an image representative of the blood flow.

58 Claims, 7 Drawing Sheets

METHOD AND APPARATUS COMBINING DIAGNOSTIC ULTRASOUND WITH THERAPEUTIC ULTRASOUND TO ENHANCE THROMBOLYSIS

STATEMENT AS TO GOVERNMENT RIGHTS

This invention was made with United States Government support under Grant Nos. 2 R44 HL 57108-02 and R43 HL 65074-01 awarded by National Institutes of Health (NIH). The United States Government has certain rights in the invention.

TECHNICAL FIELD

This invention relates generally to medical diagnostic and therapeutic procedures and devices, and more particularly, to an ultrasound method and apparatus that combines diagnostic ultrasound with therapeutic ultrasound that enhances thrombolysis.

BACKGROUND OF THE INVENTION

Thrombosis in the cardiovascular system, particularly of the arteries, veins and heart, causes many ailments, for example, stroke, heart attacks, claudication, deep vein thrombosis, and pulmonary embolism. In particular, stroke clearly compromises quality of life for its victims and for society at large. In economic terms, the total cost of stroke reaches billions of dollars each year. Direct costs include costs associated with hospital and nursing home stays, treatment by physicians and health professionals, drugs, and home health costs and other medical durables. Indirect costs include costs resulting from lost productivity due to morbidity and lost productivity due to mortality. 1995 data for Americans age 40 and older showed the average in-hospital and physician costs were $11,010 for a stroke and $4,940 for trans-ischemic attack (TIA).

Technological advances in the last 60 years to understand and prevent strokes have included angiography, association of carotid disease with cerebral infarcts, carotid endarterectomy surgery, prosthetic heart valves, Doppler ultrasound as a diagnostic modality, use of aspirin to prevent clotting, computed tomography (CT) scanning for differential diagnosis, transcranial Doppler (TCD), and stents for treating arterial lesions. None of the many major advances prior to 1995 were in the realm of direct therapy for stroke at its initiation—it was not until 1995 that techniques involving the administration of thrombolytic agents such as tissue plasminogen activators (t-PA) were shown effective in reducing neurologic damage.

There are two common types of stroke. Embolic occlusion generally accounts for 80% of all strokes, and its treatment is grossly different than that for intracerebral hemorrhage (ICH). The origins of embolic stroke are broadly divided into several categories: thrombus dislodged from a variety of sources including ulcerated carotid or aortic plaque, thrombus of cardiac origin, and thrombus of paradoxical origin from the venous system.

Initial diagnosis of stroke requires radiologic imaging techniques, such as CT or magnetic resonance imaging (MRI), to differentiate between embolic and ICH stroke and to determine the volume of tissue which has had ischemic injury. Generally, a stroke patient is a candidate for thrombolytic therapy if ICH is ruled out, and CT or MRI determines that ischemic changes do not exceed a third of the middle cerebral artery (MCA) territory, blood pressure is normal or controllable, and the diagnosis is made within three hours of onset. Widespread adoption of t-PA therapy under these circumstances has not occurred, however, because hospitals in the United States do not emphasize urgent treatment of stroke patients, and public awareness of the urgent need for medical intervention in stroke is not high. Additionally, there is a shying away from t-PA therapy due to a ten-fold increased risk of ICH, even though this risk is not associated with an overall increase in mortality. All told, only approximately 2% of those stroke patients eligible for t-PA therapy receive it.

Although ultrasound has been available as a diagnostic modality to assess cerebral hemodynamics, and although research in recent years has shown that ultrasound as a therapeutic modality for non-transcranial applications can enhance clot lysis when used in the presence of t-PA, it is not standard practice to use ultrasound to monitor cerebral blood flow during the early stages of stroke or to use ultrasound to treat stroke victims. One reason for the lack of use is due to the high skill level required to acquire and interpret TCD signals using equipment presently on the market and in clinical use. This skill level is not generally available in hospital emergency rooms. There is also a lack of appreciation for TCD capabilities in triage and monitoring. For example, the use of ultrasound monitoring to determine the point in time at which thrombolytic therapy re-establishes perfusion (e.g., blood flow through a vessel) is not fully appreciated.

Another reason for the lack of use of ultrasound is that existing instruments cannot conveniently transmit both diagnostic/monitoring and therapeutic ultrasound. Ultrasound is widespread for diagnosis of these illnesses associated with thrombosis, and a device which performs this diagnostic and the new therapeutic modalities would be of clinical use. That is, standard ultrasound instruments are designed solely for transmission of diagnostic/monitoring ultrasound at a given frequency range and cannot be easily switched to therapeutic applications that may require drastically different frequency ranges, lengths of time of application, beam profiles/coverage, or power levels. Accordingly, not only is there is a need for an ultrasound instrument that can be operated by emergency room personnel and that presents easily-interpreted diagnostic blood flow information, but also there is a need for an ultrasound instrument that can be concurrently used to therapeutically treat stroke patients (as well as individuals suffering other types of thrombosis).

SUMMARY OF THE INVENTION

A method of simultaneously treating and monitoring a patient suffering from thrombosis according to one aspect of the invention includes positioning a single ultrasound probe proximate a body surface of the patient and administering pulsed ultrasound from the single probe to the patient at a first frequency for a first period of time during a diagnostic mode. The method also includes, during a therapeutic mode, administering ultrasound from the single probe to the patient at a second frequency for a second period of time greater than the first period of time to enhance a thrombolytic action of a thrombolytic agent. The method also allows for simultaneous application of diagnostic and therapeutic ultrasound, provided the diagnostic receiver can differentiate diagnostic from therapeutic ultrasound echoes.

A method of treating a patient suffering from thrombosis with ultrasound according to another aspect of the invention includes selecting a region on a body surface of the patient and defining a plurality of areas within the region. The method includes administering the pulsed ultrasound from a single ultrasound probe to a first one of the areas during a diagnostic mode and evaluating a window through that first area. If the window through the first area is not an optimum window, the method further includes relocating the single ultrasound probe and administering the pulsed ultrasound to a second one of the areas in the diagnostic mode and evaluating a window through the second area, with at least a portion of the second area including at least a portion of the first area. The method then repeats administering the pulsed ultrasound to another area in the diagnostic mode if prior areas administered with pulsed ultrasound do not substantially include the optimum window, until an area having substantially the optimum window is located, and then administers the ultrasound in the therapeutic mode from the single ultrasound probe through the area having substantially the optimum window.

Still another aspect of the invention provides an apparatus to treat a patient suffering from thrombosis with ultrasound by enhancing a thrombolytic action of a thrombolytic agent. The apparatus comprises a single ultrasound probe structured to transmit pulsed or continuous-wave ultrasound both in a therapeutic mode and pulsed ultrasound in a diagnostic mode, the ultrasound having a characteristic in the therapeutic mode that is different from a characteristic of the pulsed ultrasound in the diagnostic mode. A controller is structured to switch the single ultrasound probe between the diagnostic and therapeutic modes and to process ultrasound Doppler signals returned by the single ultrasound probe during the diagnostic mode. A graphical display is responsive to the controller and coupled to the single ultrasound probe. The graphical display has a blood locator display structured to depict a plurality of locations along an ultrasound beam axis at which blood flow is detected. The blood locator display is responsive to the controller to depict the plurality of locations during the diagnostic mode based on the Doppler signals.

BRIEF DESCRIPTION OF THE DRAWINGS

In the drawings, like reference numbers refer to similar elements or steps.

DETAILED DESCRIPTION OF THE ILLUSTRATED EMBODIMENTS

Embodiments of the present invention provide a Doppler ultrasound method and device that monitors cerebral blood flow velocity and concurrently enhances the lysing effect of thrombolytic agents, such as t-PA or urokinase. These embodiments are particularly useful in connection with hospital emergency services. With respect to transcranial applications, embodiments of the invention provide a TCD modality that exists for real-time detection of cerebral blood flow during the early stages of stroke. While embodiments of the invention are generally described herein in the context of transcranial applications, the invention is not limited to this particular application. It will be appreciated that some or all of the principles of the present invention can be applied to cardiac and other components of the cardiovascular system, such as the heart, pulmonary artery and the deep veins of the legs, of a patient affected by thrombosis.

Certain details are set forth to provide a sufficient understanding of the invention. However, it will be clear to one skilled in the art that the invention may be practiced without these particular details. In other instances, well-known circuits, control signals, timing protocols, and software operations have not been shown or described in detail in order to avoid unnecessarily obscuring the invention.

Treatment of a Patient

Figure 1:
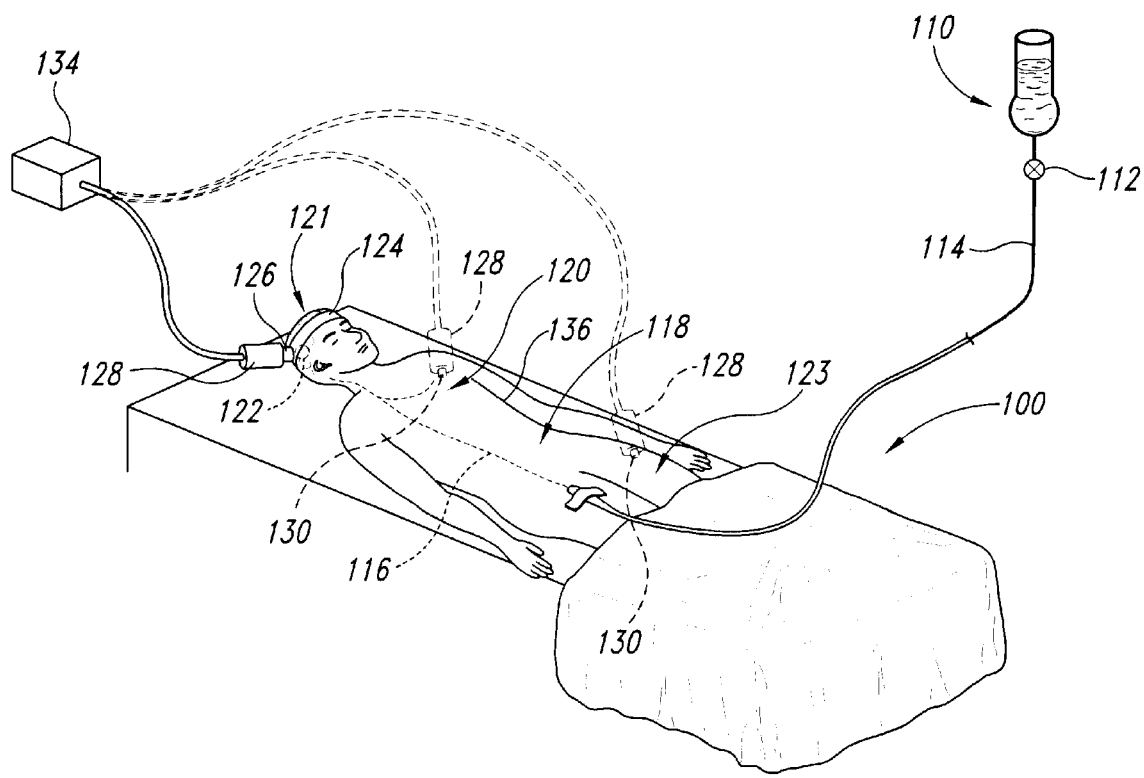
FIG. 1 is an isometric view of an embodiment of an apparatus and method that combines diagnostic ultrasound with therapeutic ultrasound according to the principles of the present invention.

Referring first to FIG. 1, a method and/or apparatus 100 in accordance with an embodiment of the present invention for combining diagnostic ultrasound with therapeutic ultrasound is shown. A vial 110 having a thrombolytic agent (such as t-PA, recombinant t-PA or rt-PA, TNK t-PA, urokinase, or streptokinase) is administered to a patient via a valve 112 and a catheter 114. The catheter 114 injects, introduces, or delivers the thrombolytic agent to a vessel 116 within a body 118 of the patient. Although the thrombolytic agent is shown in FIG. 1 as being introduced into the body 118 via a catheter 114, it is to be appreciated that the thrombolytic agent can be injected proximate a thrombosis in any conventional manner, including, for example, via hypodermic needles, while the ultrasound is delivered to the site of the thrombus.

As illustrated in FIG. 1, the vessel 116 carries the thrombolytic agent to a thrombosis 122 located in the cranial region 121, such as when the patient has suffered a stroke. In alternative applications of the method and apparatus 100, the catheter 114 can be positioned within the body 118 such that the vessel 116 carries the thrombolytic agent near a cardiac region 120 in order to treat a thrombosis located in the cardiac region. Similarly, the thrombolytic agent may administered to a leg region 123 of the body 118 in order to treat thrombosis in the deep veins of the leg.

Following the administration of a thrombolytic agent into the body 118, an ultrasound probe 128 is positioned proximate to a region of the body 118 of the patient where the thrombosis is present. For example, FIG. 1 shows the probe 128 positioned near the cardiac region 120 in order to radiate a thrombosis in that respective region, such as in the heart or pulmonary artery. The probe 128 may be alternatively positioned near the leg region 123 of the body 118 in order to radiate a thrombosis in that region. FIG. 1 further illustrates the probe 128 positioned near the cranial region 121. In a particular embodiment, during transcranial administration of ultrasound to the patient, a head frame 124 is fitted over the cranial region 121 of the patient. The head frame 124 includes a mounting attachment 126 structured to hold an ultrasound transducer or probe 128 in place. As mentioned previously, the thrombolytic agent may also be administered and the ultrasound probe 128 may be positioned proximate to other regions of the body 118 where a thrombosis may exist.

The probe 128 includes a tip 130 that allows ultrasound to be applied transcutaneously or transdermally through a body surface 136. Specific structural details and associated operating features of the probe 128 will be described in further detail below. The probe 128 is coupled to a driver 134, which can have an adjustable power output ranging from a few milliwatts to a few watts. The driver 134 and the probe 128 may be operated such that ultrasound is transmitted at a duty cycle of 100% (e.g., a continuous wave) or pulse-operated at various duty cycles (e.g., at 3% to 80% duty cycles, for example). Embodiments of the invention provide pulsed or continuous wave diagnostic and pulsed or continuous wave therapeutic ultrasound. Pulsed diagnostic and pulsed therapeutic ultrasound are discussed in this particular embodiment, but one skilled in the art will understand that continuous wave can alternatively be used. In the "diagnostic" mode of the embodiment described below, pulsed ultrasound provides the advantage over continuous-wave of enabling easy spatial discrimination of the blood flow of interest. This diagnostic advantage of pulsed ultrasound is elaborated below.

Although FIG. 1 shows that the thrombolytic agent is externally administered from a vial 110, it is also possible to practice embodiments of the invention without administering an external thrombolytic agent. Such embodiments take into account the fact that the human body contains naturally occurring thrombolytic agents in body fluids. Although the concentration of naturally occurring thrombolytic agents is less than a concentration that would be obtained if an external thrombolytic agent is applied, embodiments of the present invention can still use therapeutic ultrasound to enhance the thrombolytic action of the naturally occurring thrombolytic agents.

Ultrasound Probe and Corresponding Ultrasound Beams

Figure 2:
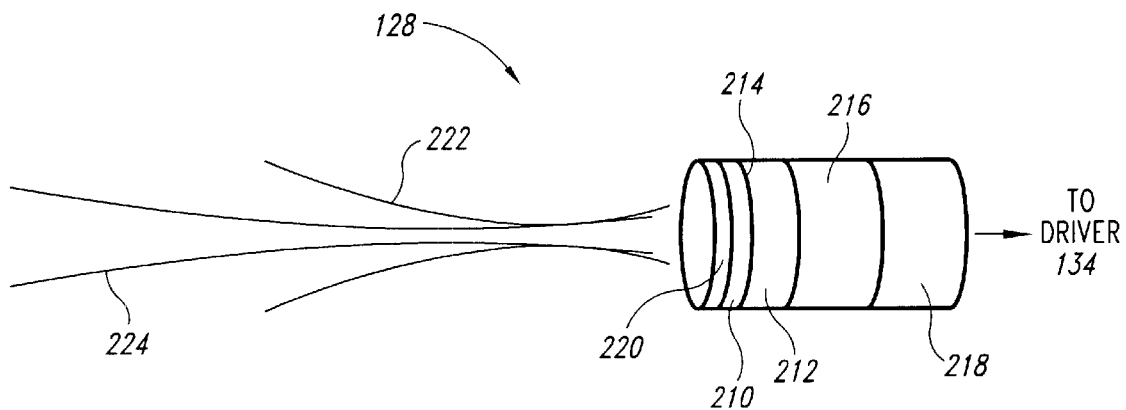
FIG. 2 is a diagram showing a first embodiment of an ultrasound probe used in the apparatus of FIG. 1.

FIG. 2 shows an embodiment of the probe 128 that can be used to apply two different ultrasound frequencies to the patient. The embodiment of the probe 128 shown in FIG. 2 is used to transmit ultrasound frequencies of approximately 2 MHz during a diagnostic mode to monitor blood flow and 200 kHz during a therapeutic mode to enhance the thrombolytic action of the thrombolytic agent.

The probe 128 comprises two transducer elements, namely, a 2 MHz crystal 210 and a 200 kHz crystal 212. A dielectric layer 214 separates the crystals 210 and 212. The probe 128 further comprises a damping layer 216 and a potting layer 218, with the damping layer 216 and the potting layer 218 being disposed on the driver-end of the probe 128. A matching layer 220 is disposed on the patient-end of the probe 128.

The embodiment of the probe 128 shown in FIG. 2 is thus a "dual frequency stack" configuration in which the crystal 210 functions as a transducer having a bandwidth range in the vicinity of 2 MHz. Directly behind the crystal 210 is the crystal 212 functioning as a transducer having a bandwidth range in the vicinity of 200 kHz. Other frequency pairs besides 2 MHz and 200 kHz can be transmitted by choosing probes 128 having crystals with different frequency ranges. For example, a frequency pair of 100 kHz and 2 MHz or a frequency pair of 1 MHz and 2 MHz can be transmitted. Further, different frequency pairs can be transmitted by adjusting the frequency output of the driver 134 such that the output frequencies of the crystals 210 and 212 are slightly varied from their respective 2 MHz and 200 kHz design frequencies. Thus, a frequency pair of 180 kHz and 2 MHz can be transmitted.

The crystals 210 and 212 can have a diameter of 13 mm, although other diameters, not necessarily equal to each other, can be used depending on the desired focal diameter of the ultrasound beams 222 and 224. The probe 128 shown in FIG. 2 is custom-made for the diagnostic and therapeutic ultrasound applications described herein and is available from Etalon, Inc. of Lebanon, Ind. Further, the impedances of the various components 210–220 of the probe 128 stack can be designed with matching impedances so as to maximize power transfer and to minimize losses between the components.

As described above, the probe 128 shown in FIG. 2 can produce two ultrasound beams 222 and 224 having different frequencies and shapes. The therapeutic beam 222 having a low frequency is transmitted from the crystal 212. The diagnostic beam 224 having a high frequency is transmitted from the crystal 210. The diagnostic beam 224 has a narrower focus or beam shape of the two beams in order to optimize the lateral spatial resolution of the diagnostic beam 224. The therapeutic beam 222 has a wider focus in order to maximize the effective radiation area of the beam in the vicinity of a thrombosis.

Figure 3:
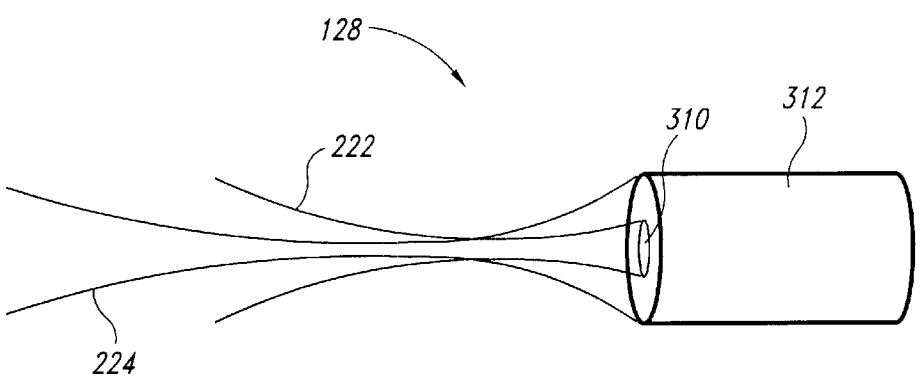
FIG. 3 is a diagram of a second embodiment of an ultrasound probe that may be used in the apparatus of FIG. 1.

An alternative embodiment of the probe 128 is shown in FIG. 3. This embodiment produces therapeutic and diagnostic beams 222 and 224, respectively, both having the same frequency of 2 MHz (or other frequency). The probe 128 comprises two transducer elements annularly arranged into a 7-mm diameter piston transducer element 310 surrounded by an annulus transducer element 312 having an outer diameter of 13 mm. This concentric shape allows the probe 128 to be fired on both elements (e.g., the piston 310 and the annulus 312) and received on both elements when performing diagnostic measurements of blood flow using the diagnostic beam 224. Only the piston 310 is fired when transmitting the therapeutic beam 222 at 2 MHz. The piston 310 transmits a broader therapeutic beam 222 when activated as a single element during the therapeutic mode. When both the piston 310 and the annulus 312 are activated during the diagnostic mode, the two elements combined transmit the narrower diagnostic beam 224.

In summary, the embodiment of the probe 128 in FIG. 2 can operate in two frequency regimes to transmit two ultrasound beams having different profiles. For the alternative embodiment of the probe 128 shown in FIG. 3, the same frequency is transmitted by the probe 128 for both diagnostic and therapeutic applications, but the configuration of the probe 128 allows the ultrasound beams 222 and 224 to also have two different shapes. As will be described below, the frequencies, number of cycles, intensity, duty cycle, and resulting temporal peak intensity for the ultrasound beams 222 and 224 transmitted by both embodiments of the probe 128 can be varied in order to facilitate an optimum set of parameters to enhance thrombolysis in a particular venue of the body.

Administering Therapeutic Ultrasound

Embodiments of the invention administer therapeutic ultrasound to enhance the lysing effect of a thrombolytic agent. Three mechanisms by which ultrasound can potentially enhance thrombolysis in the presence of a thrombolytic agent like t-PA are: "cavitation" (the formation of a bubble via negative pressure, which can in turn cause localized fluid motion), "streaming" and "microstreaming" (conversion of propagating ultrasound energy into fluid motion within tissue), and reversible change of fibrin structure. The latter mechanism decreases fibrin matrix flow resistance and increases fibrin binding sites for t-PA. The frequencies of this therapeutic ultrasound can be different for these different underlying mechanisms.

A feature of embodiments of the present invention is that therapeutic ultrasound at higher frequencies (e.g., at 2 MHz) can be used effectively to enhance thrombolysis. This is in direct contrast to conventional approaches that have advocated the use of lower frequencies. Therapeutic ultrasound in the present invention is administered in alternating time periods with diagnostic ultrasound. The therapeutic time periods are generally long (~1 minute), after which diagnostic ultrasound is used for a brief (~4 seconds) period to monitor therapeutic progress.

Additionally, pulsed ultrasound is performed in vivo at low power levels, such as an average intensity of 50 mW/cm$^2$ or less, with an intensity level and mode presumed to not induce cavitation or significant streaming. The use of low power levels is also in contrast to low frequency literature reports that explore continuous wave ultrasound at high power, in vitro, and that do not utilize transcranial monitoring and treatment from the same probe. Spatial peak temporal average ultrasound intensity levels for embodiments of the present invention adhere to industry-agreed upon diagnostic levels to not exceed 720 mW/cm$^2$ (this is a derated measurement made in water). It will be appreciated that an ultrasound beam with this derated intensity in water will have a much lower intensity in the application of the ultrasound to the middle cerebral artery. The lower intensity level is due to reflection and attenuation loss that occurs at the temporal bone, in addition to the attenuation loss through brain tissue. Rudimentary calculations using bone attenuation of 40 dB/cm at 2 MHz, brain tissue attenuation of 0.5 dB/cm at 2 MHz, and assuming 3 mm bone thickness and 5 cm of brain tissue show the resulting intensity to be less than 50 mW/cm$^2$.

Administering Diagnostic Ultrasound

Embodiments of the invention allow diagnostic ultrasound at 2 MHz to be administered concurrently with therapeutic ultrasound. The diagnostic mode of an embodiment of the present invention provides an information display in connection with Doppler ultrasound monitoring of blood flow, such as that described in greater detail in copending U.S. patent application Ser. No. 09/190,402 entitled "DOPPLER ULTRASOUND METHOD AND APPARATUS FOR MONITORING BLOOD FLOW," filed Nov. 11, 1998, now pending and incorporated by reference.

Figure 4:
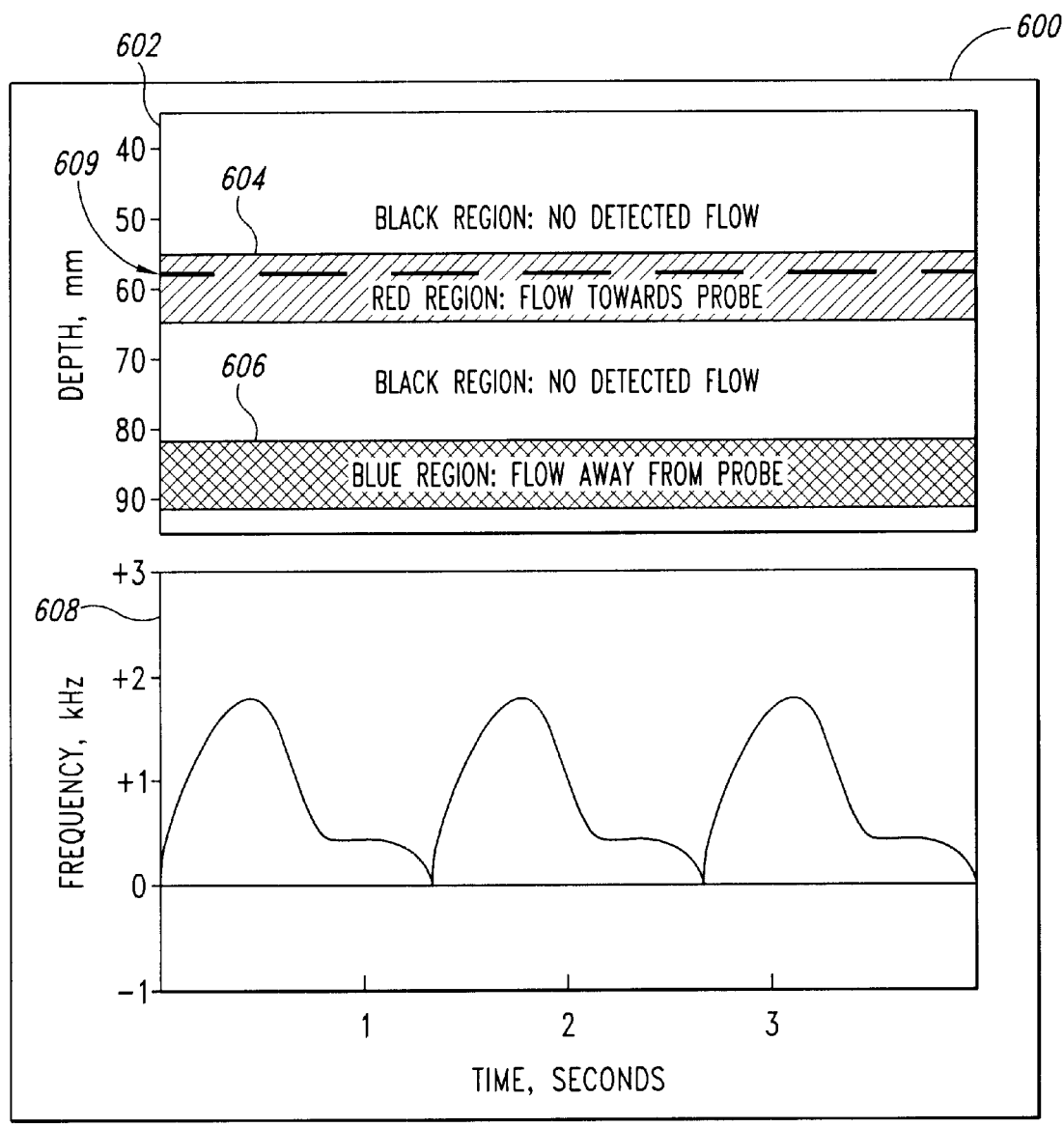
FIG. 4 is a graphical diagram depicting a Doppler ultrasound system display mode in accordance with an embodiment of the invention.

FIG. 4 is a graphical diagram depicting a first embodiment of a display mode 600 of Doppler ultrasound information in accordance with one aspect of the invention. This display mode 600 is used in connection with aiming the probe 128. In this display mode 600, one or both of two distinct ultrasound displays are provided to the user. A depth-mode display 602 depicts, with color, blood flow away from and towards the ultrasound probe 128 at various depths along the ultrasound beam axis (vertical axis) as a function of time (horizontal axis).

The depth-mode display 602 includes colored regions 604 and 606. Each region is colored either red or blue, where red indicates flow towards the probe 128 and blue indicates flow away from the probe. The colored regions are not of uniform color, with the intensity of color varying as a function of the detected intensity of the return Doppler ultrasound signal.

Figure 6:
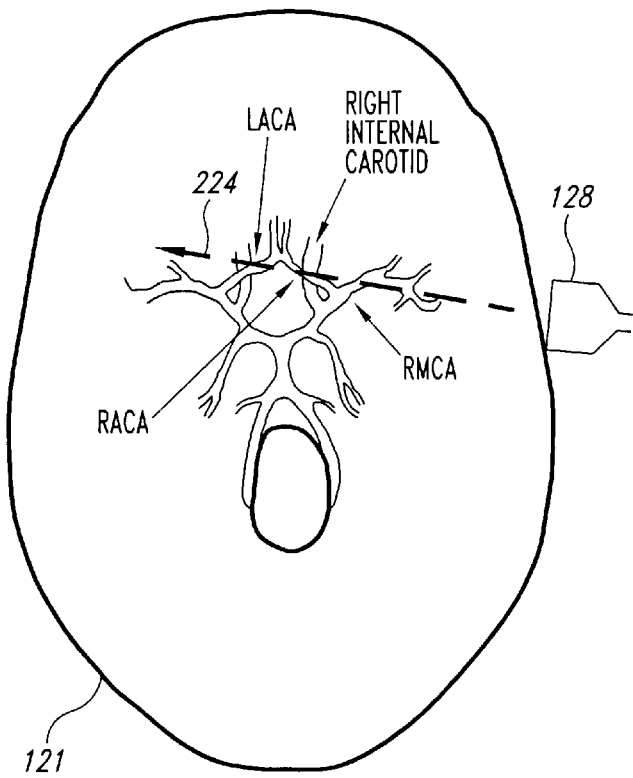
FIG. 6 is an anatomical schematic of a cranial region of a patient.

The display mode 600 can include a displayed spectrogram 608, with FIG. 6 depicting a velocity envelope showing the characteristic systolic-diastolic pattern. Like the depth-mode display 602, the spectrogram 608 includes data points (not shown) within the velocity envelope that are colored in varying intensity as a function of the detected intensity of the return ultrasound signal. The particular sample volume for which the spectrogram 608 applies is at a depth indicated in the depth-mode display 602 by depth indicator or pointer 609. In this way, a user of the ultrasound apparatus 100 can conveniently see and select particular depths at which to measure the spectrogram 608. The depth-mode display 602 readily and conveniently provides the information concerning the range of appropriate depths at which a meaningful spectrogram may be obtained.

As described above, the color intensity of regions 604 and 606 can vary as a function of the detected intensity of the return ultrasound signal. Filtering techniques, such as clutter filtering, can also be utilized in order to avoid displaying spurious information associated with signals that may be intense but low velocity (such as that due to tissue motion) or with signals having low power (such as that due to noise).

While the embodiment of the depth-mode display 602 employs color intensity mapping as a function of signal intensity, and is further colored red or blue according to flow directions towards or away from the probe 128, those skilled in the art will appreciate that color intensity as a function of detected velocity may be employed instead. Those skilled in the art will also appreciate that instead of varying color intensity solely as a function of signal amplitude, or solely as a function of velocity, one could advantageously vary color intensity as a function of both signal amplitude and velocity, or use some other data presentation.

The particularly depicted depth-mode display 602 shows a simplified display of a single, well-defined red region 604, and a single, well-defined blue region 606. Those skilled in the art will appreciate that the number and characteristics of colored regions will vary depending on the placement and orientation of the probe 128. Indeed, a catalogue of characteristic depth-mode displays can be provided to assist the user in determining whether a particularly desired blood vessel has, in fact, been located. Once the user finds the characteristic depth-mode display for the desired blood vessel, the user can then conveniently determine the depth at which to measure the spectrogram 608.

The display mode 600 enables the user to quickly position the ultrasound probe 128, such as adjacent to an ultrasound window through the skull (or cranial region 121) so that intracranial blood flow can be detected. This procedure will be described later below with reference to FIGS. 9 and 10. Use of a colorized representation of signal amplitude is particularly advantageous for this purpose, since a strong signal is indicative of good probe location and orientation. That is, the diagnostic beam 224 is well aimed as the color intensity increases with a volume of moving blood and with the speed of the blood, which as a general rule, occurs when the diagnostic beam is centered on the blood flow.

Figure 5:
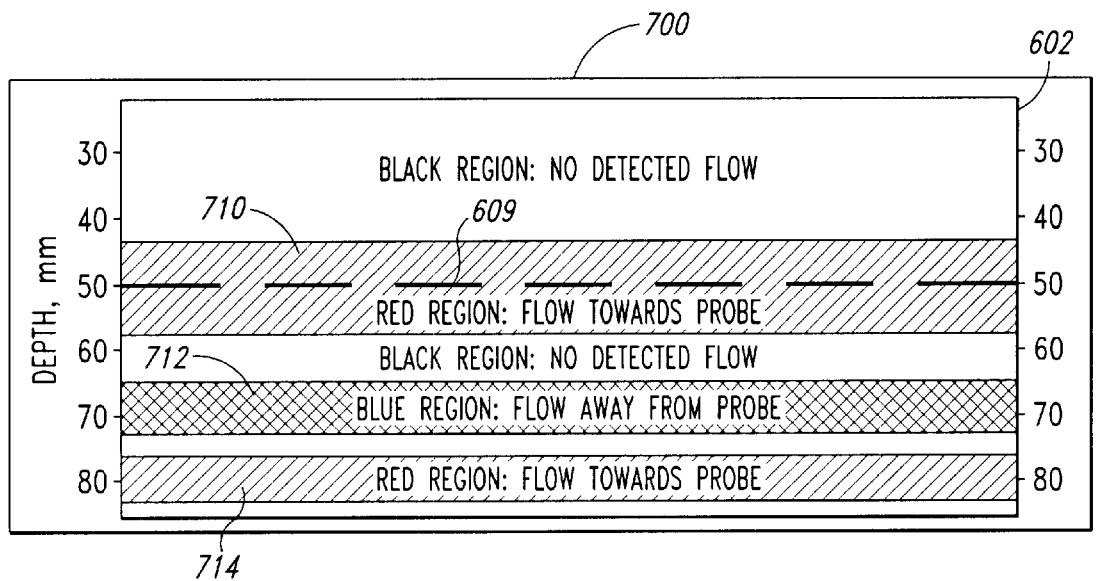
FIG. 5 is a graphical diagram depicting an alternative embodiment of a Doppler ultrasound system display mode in accordance with an embodiment of the invention.

FIG. 5 shows a second, alternative embodiment of a display mode 700, which is to be viewed in conjunction with an anatomical schematic of the cranial region 121 of FIG. 6. The display mode 700 has particular usefulness when viewing blood flow in the cranial region 121 (e.g., a patient suffering from a stroke), although the embodiment shown in FIG. 4 can also be used. Unlike the display mode 600, the display mode 700 only includes the depth-mode display 602 and does not have a spectrogram 608. By expanding the depth-mode display 602 to fill the entire display and eliminating the spectrogram 608 (which requires greater skill to understand than does the depth-mode display), a simplified user interface is provided for observing middle cerebral circulation by emergency room personnel who do not have expertise in ultrasound.

Simultaneous observation of multiple vessels in the middle cerebral circulation is possible with the display mode 700. For example, in FIG. 6 there are three vessels aligned with the axis of the diagnostic beam 224: the right middle cerebral artery (RMCA), the right anterior cerebral artery (RACA), and the left anterior cerebral artery (LACA). FIG. 5 shows three regions 710, 712, and 714, similar to the regions 604 and 606 shown in the display mode 600 of FIG. 4. The regions 710, 712, and 714 represent blood flow in the RMCA, RACA, and LACA, respectively, at various depths along the beam axis of the diagnostic beam 224. For instance, the region 710 shows blood flow in the RMCA at a 50-mm gate depth, centered along the pointer 609. Similar to the regions 604 and 606, the regions 710, 712, and 714 have red or blue colors of varying intensities to represent signal intensity, blood flow velocity, a combination of both, or some other representation of data.

Thus, a color m-mode Doppler allows a user to view blood flow at all depths along the beam axis concurrently, rather that at one depth at a time. This advantage over single-gate Doppler instruments shortens the time to locate a window through the temporal bone, through which the flow of blood may be observed. Further, blood flow that may be missed due to incorrect gate depth setting for a single gate Doppler will not be missed by the display mode 700. Additionally the m-mode is used for localizing occluded vessels where only signals in the region surrounding occluded vessel are appreciated.

System for Combined Diagnostic and Therapeutic Ultrasound

Figure 7:
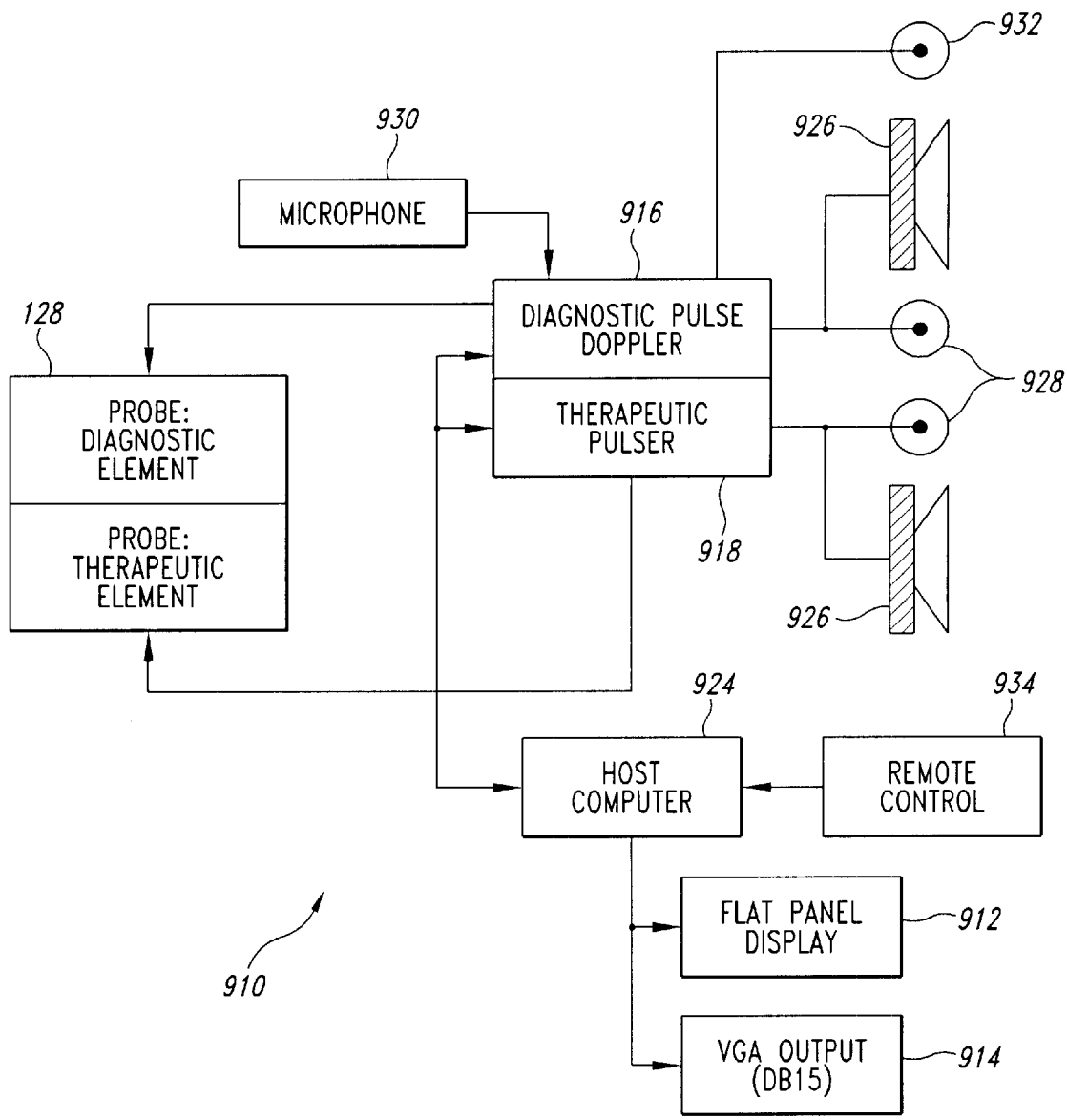
FIG. 7 is a functional block diagram depicting a Doppler ultrasound system in accordance with an embodiment of the invention.

FIG. 7 is a functional block diagram that depicts an ultrasound system 910 in accordance with an embodiment of the invention. The ultrasound system 910 produces the various display modes 600 and 700 described above in connection with FIGS. 4 and 5 on an integrated flat panel display 912, or other desired display format via a display interface connector 914. The signal-processing core of the Doppler ultrasound system 910 is a diagnostic pulse Doppler circuit 916 and a therapeutic pulser circuit 918. During the diagnostic mode, only the diagnostic pulse Doppler circuit 916 is enabled. During the therapeutic mode, the diagnostic pulse Doppler circuit 916 and the therapeutic pulser circuit 918 may both be enabled simultaneously. The Doppler probe 128 is coupled to the diagnostic pulse Doppler 916 and therapeutic pulser circuit 918. By providing both the diagnostic pulse Doppler and therapeutic pulser circuits 916 and 918, the ultrasound system 910 can switch between two separate modes (e.g., a diagnostic mode and a therapeutic mode). The diagnostic pulse Doppler circuit 916 receives the ultrasound signals detected by the probe 128 and performs signal and data processing operations, as will be described in detail below. Data is then transmitted to a general-purpose host computer 924 that provides data storage and display. A suitable host computer 924 is a 200 MHz Pentium processor-based system having display, keyboard, internal hard disk, and external storage controllers, although any of a variety of suitably adapted computer systems may be employed. While this embodiment utilizes alternating applications of diagnostic and therapeutic ultrasound, one skilled in the art will also appreciate that the invention may also be practiced using simultaneous applications of diagnostic and therapeutic ultrasound if the diagnostic receiver can differentiate diagnostic from therapeutic ultrasound reflections.

The ultrasound system 910 also provides Doppler audio output signals via audio speakers 926, as well as via audio lines 928 for storage or for output via an alternative medium. The ultrasound system 910 also includes a microphone 930 for receipt of audible information input by the user. This information can then be output for external storage or playback via a voice line 932. The user interfaces with the ultrasound system 910 primarily via a keyboard or other remote input control unit 934 coupled with the host computer 924.

As mentioned previously, operation of the ultrasound system 910 may be performed automatically by programming the host computer 924 to perform such tasks, such as controlling the administration of diagnostic and therapeutic ultrasound. As will be explained in greater detail below, a probe 128 having a plurality of transducer elements arranged in an array can be used to locate an optimal probe position for therapeutic ultrasound. The host computer 924 can be programmed with suitable pattern recognition software to take advantage of such a probe. After locating the optimal window for administering the ultrasound, the host computer 924 switches to therapeutic mode and administers the therapeutic ultrasound. Additional programming of the host computer 924 for automated operation of the ultrasound system 910 is well known in the art.

Figure 8:
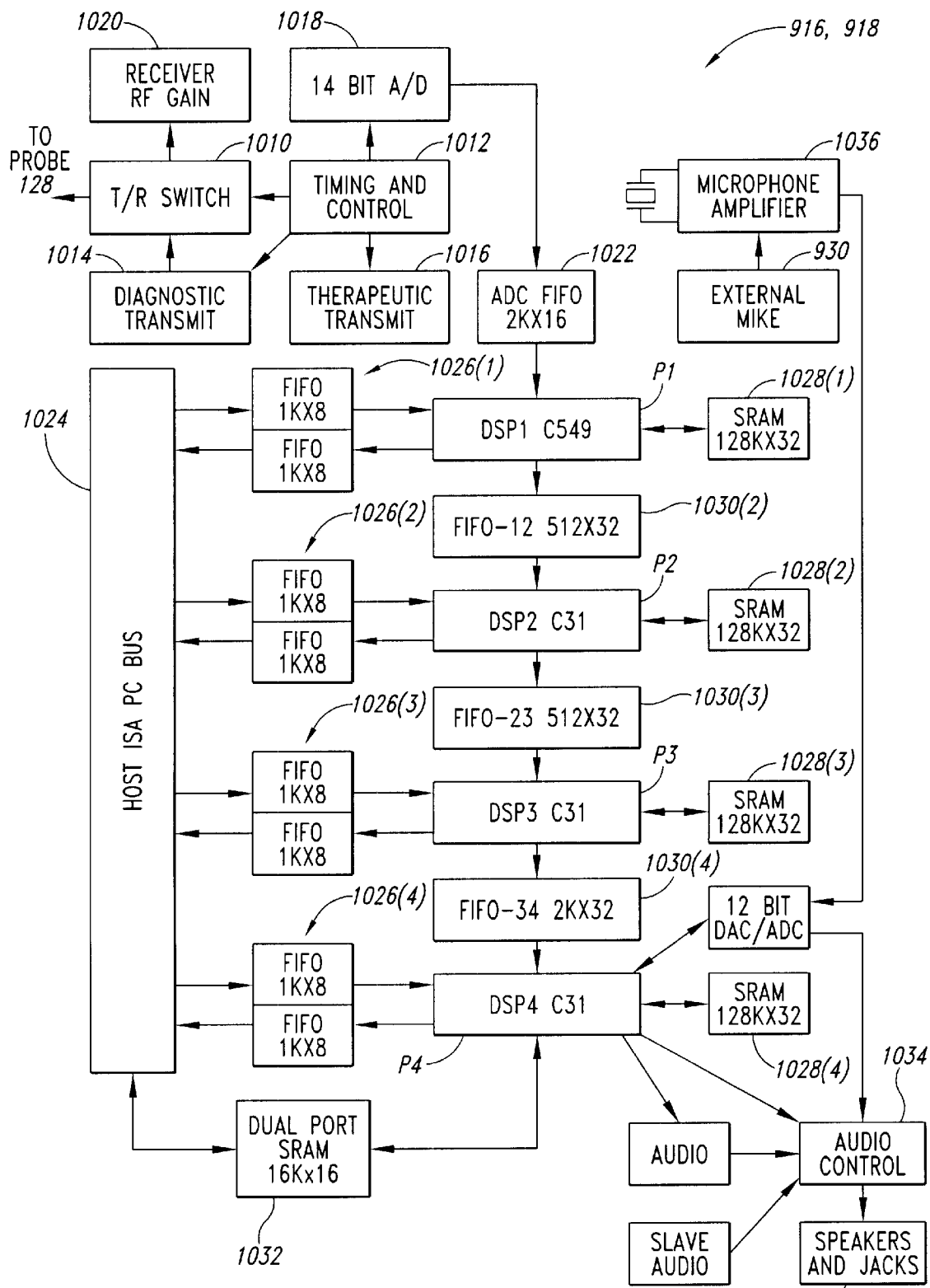
FIG. 8 is a functional block diagram depicting particular details of pulse Doppler signal processing circuitry included in the Doppler ultrasound system of FIG. 9.

FIG. 8 depicts particular details of the diagnostic pulse Doppler and therapeutic pulser circuits, hereinafter also referred to as the "combined pulser circuit" 916. FIG. 8 also depicts details concerning the input and output of audio information to and from the ultrasound system 910 via the microphone 930, the speakers 926, and the audio output lines 928 and 932, the operations of which are controlled by the diagnostic pulse Doppler circuit 916.

At the probe 128 input/output stage, the master pulse Doppler circuit 916 includes a transmit/receive switch circuit 1010 operating under control of a timing and control circuit 1012. The particular timing of operations by the diagnostic pulse Doppler circuit 916 and the therapeutic pulser circuit 918 are controlled by the timing and control circuit 1012 of the diagnostic pulse Doppler circuit 916.

The timing and control circuit 1012 also controls operation of a diagnostic transmit circuit 1014 (on the master card) that provides an output drive signal that causes the probe 128 to emit the pulsed, ultrasound diagnostic beam 224 during the diagnostic mode. The timing and control circuit 1012 further controls operation of a therapeutic transmit circuit 1014 that provides an output drive signal to cause the probe 128 to emit the pulsed ultrasound, therapeutic beam 222 during the therapeutic mode. The timing and control circuit 176 additionally controls an analog-to-digital converter circuit 1018 coupled to the transmit/receive switch 1010 by a receiver circuit 1020. The function and operation of circuits 1010–1020 are well known to those skilled in the art and need not be described further herein.

The primary signal processing functions of the diagnostic pulse Doppler circuit 916 are performed by four digital signal processors P1–P4. P1 is at the front end and receives digitized transducer data from the receiver circuit 1020 via the analog-to-digital converter circuit 1018 and a data buffer or first-in-first-out (FIFO) circuit 1022. P4 is at the back end and performs higher level tasks such as final display preparation. A suitable digital signal processor for P1 is a Texas Instruments TMS320LC549 integer processor, and suitable digital signal processors for P2–P4 are Texas Instruments TMS320C31 floating point processors, although other digital signal processing circuits may be employed to perform substantially the same functions in accordance with embodiments of the invention.

Received ultrasound signals are first processed by the digital signal processor P1 and then passed through the signal-processing pipeline of the digital signal processors P2, P3, and P4. As described in greater detail in co-pending U.S. patent application Ser. No. 09/190,402 identified above, the digital signal processor P1 constructs quadrature vectors from the received digital data, performs filtering operations, and outputs Doppler shift signals associated with 64 different range gate positions. The digital signal processor P2 performs clutter cancellation at all gate depths. The digital signal processor P3 performs a variety of calculations, including autocorrelation, phase, and power calculations. P3 also provides preparation of the quadrature data for stereo audio output. The digital signal processor P4 performs most of the calculations associated with the spectrogram display and also prepares final calculations associated with preparation of the display modes 600 or 700.

Each of the digital signal processors P1–P4 is coupled with the host computer 924 (see, e.g., FIG. 7) via a host bus 1024 and control data buffer circuitry, such as corresponding FIFOs 1026(1)–1026(4). This buffer circuitry allows initialization and program loading of the digital signal processors P1–P4, as well as other operational communications between the digital signal processors P1–P4 and the host computer 924. Each of the digital signal processors P1–P4 is coupled with an associated high-speed memory or SRAM 1028(1)–1028(4), which function as program and data memories for the associated signal processors. If the digital signal processor PI has sufficient internal memory, no external program and data memory SRAM 1028(1) need be provided. Transmission of data from one digital signal processor to the next is provided by intervening data buffer or FIFO circuitry 1030(2)–1030(4). The ultrasound data processed by the digital signal processor P4 is provided to the host computer 924 via data buffer circuitry such as a dual port SRAM 1032.

In FIG. 8, the digital signal processor P4 of the diagnostic pulse Doppler circuit 916 also processes audio input via the microphone 930 (which may be coupled to an amplifier 1036), as well as controlling provision of the audio output signals to the speakers 926 and audio output lines 928, 932. P4 controls the audio output signals by controlling operations of an audio control circuit 1034, which receives audio signals from both the diagnostic pulse Doppler and the therapeutic pulser circuits 916 and 918.

As mentioned above, the circuit shown in FIG. 8 may be embodied in two separate cards (e.g., a master card and a slave card) but has been combined in FIG. 8 for simplicity of illustration. Where two separate cards are employed, the master card has substantially all of the elements shown in FIG. 8 except for the therapeutic transmit circuit 1016. Instead, the slave card has the therapeutic transmit circuit 1016 (which receives timing and control information from the timing and control circuit 1012 on the master card) and is itself coupled to the host computer 924 via the host bus 1024.

In operation, the diagnostic pulse Doppler circuit 916 is enabled during the diagnostic mode to transmit the diagnostic beam 224, and then to process and display the blood flow information. The therapeutic pulser circuit 918 is not enabled during the diagnostic mode. The timing and control circuit 1012 is operable to switch the ultrasound system 910 alternately between the diagnostic and therapeutic modes, such that the both the diagnostic pulse Doppler circuit 916 and the therapeutic pulser circuit 918 can be enabled during the therapeutic mode. In the therapeutic mode, timing and control circuit 1012 controls the operation of the therapeutic transmit circuit 1016 in order to transmit the therapeutic beam 222.

Locating Temporal Windows and Aiming

Figure 9:
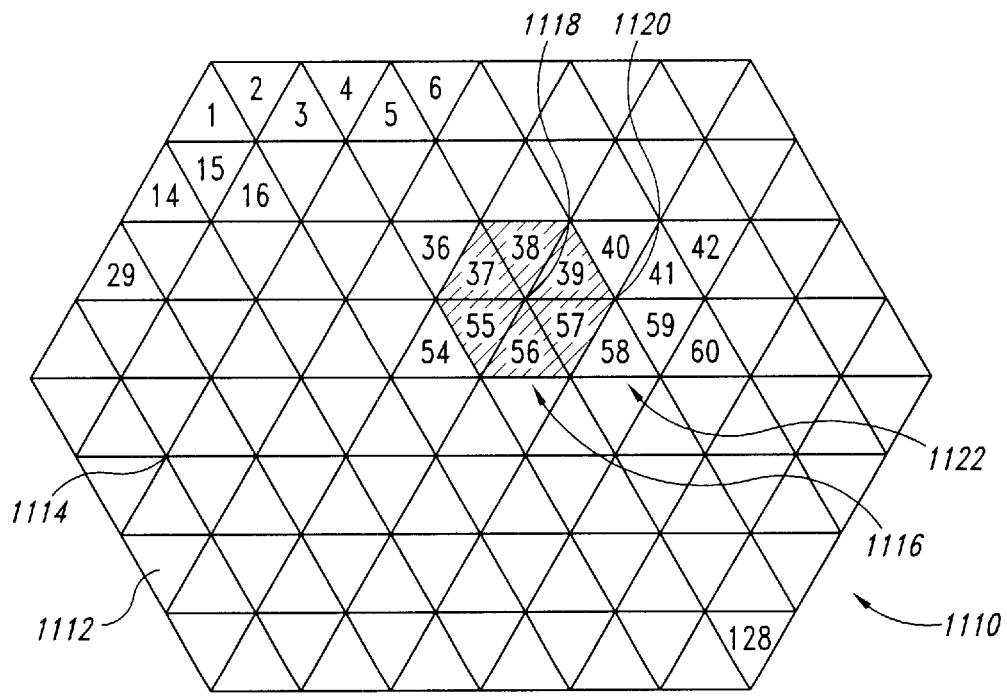
FIG. 9 is a schematic diagram of a third embodiment of an ultrasound probe used in the apparatus of FIG. 1.

FIG. 9 illustrates another embodiment of a probe 128 to be used in combining diagnostic and therapeutic ultrasound for enhanced thrombolysis. For this embodiment, the diagnostic and therapeutic frequencies are the same. The user is given the ability to locate the temporal window by selecting from a plurality of transducer elements 1112 arranged in an array which substantially cover the temporal bone region, rather than having to reposition a single probe comprised of two transducer elements, as previously described with respect to FIGS. 2 and 3. In FIG. 9, a hexagonal region 1110 is defined as the overall surface of the transducer. The region 1110 is comprised of 128 equilateral triangles, intersecting at their vertices 1114. Each triangle is a transducer element 1112. The 128 triangular transducer elements 1112 are selected for the region 1110 because of the binary nature of the number 128, and the resulting large hexagonal region maintains good coverage of the human temporal bone territory. However, it will be appreciated that the region 1110 can have any number of triangular elements 1112 by increasing or decreasing the overall size, or changing the size of the basic equilateral triangle unit. Control of the transducer elements 1112 is accomplished through the timing and control functional block 1012 and the transmit/receive switch 1010. Instead of having two transducer elements to control, as in the probes illustrated in FIGS. 2 and 3, there are a plurality of equilateral triangle elements to control—128 elements in the present example—and utilize in hexagonal groups of six.

A group of six triangular transducer elements (e.g., the triangles 37–39 and 55–57) form a hexagonal area 1116 from which the diagnostic beam 224 is initially emitted. The lengths of the sides of the triangular elements 1112 are selected such that distances between the vertices of the hexagonal area 1116 are approximately 11 mm. The 11-mm "width" of the hexagonal area 1116 is compatible with a circular probe 128 having a similar diameter of 11 mm. It will be appreciated that other sizes for the hexagonal areas may be selected for accomplishing different beam widths for a given frequency.

With the hexagonal area 1116 having a width of 11 mm, the height of the hexagonal region 1110 is approximately 38 mm. The horizontal upper and lower sides of the hexagonal region 1110 have lengths of approximately 33 mm, and its diagonal sides have lengths of approximately 22 mm.

In operation, the diagnostic beam emitted from the hexagonal area 1116 has an axis which includes a central point 1118 of the hexagonal area 1116. The resulting Doppler image of the blood flow along that axis is displayed, for example, in the display mode 700, which was previously described. If the image is unsatisfactory, indicating a poor temporal window, then the diagnostic beam emanating from point 1118 is relocated such that it is aimed from a new point (such as the point 1120) adjacent to the central point 1118.

By emitting the diagnostic beam from the point 1120, triangular elements 39–41 and 57–59, which define a new hexagonal area 1122, now become active.

An advantage of relocating the beam axis to the adjacent point 1120 is that the hexagonal area 1122 will include, or overlap, triangular elements 39 and 57 from the prior hexagonal area 1116. By overlapping the active triangular elements and sequentially aiming the diagnostic beam from one adjacent point to another, the cranial region 121 can be thoroughly administered with the diagnostic beam in order to find the best temporal window. Additionally, by overlapping triangles of adjacent hexagonal areas, a "picket fence" effect where there are gaps between Doppler images is avoided. Once the best temporal window is located, the therapeutic beam is transmitted from the same hexagonal region.

Figure 10:
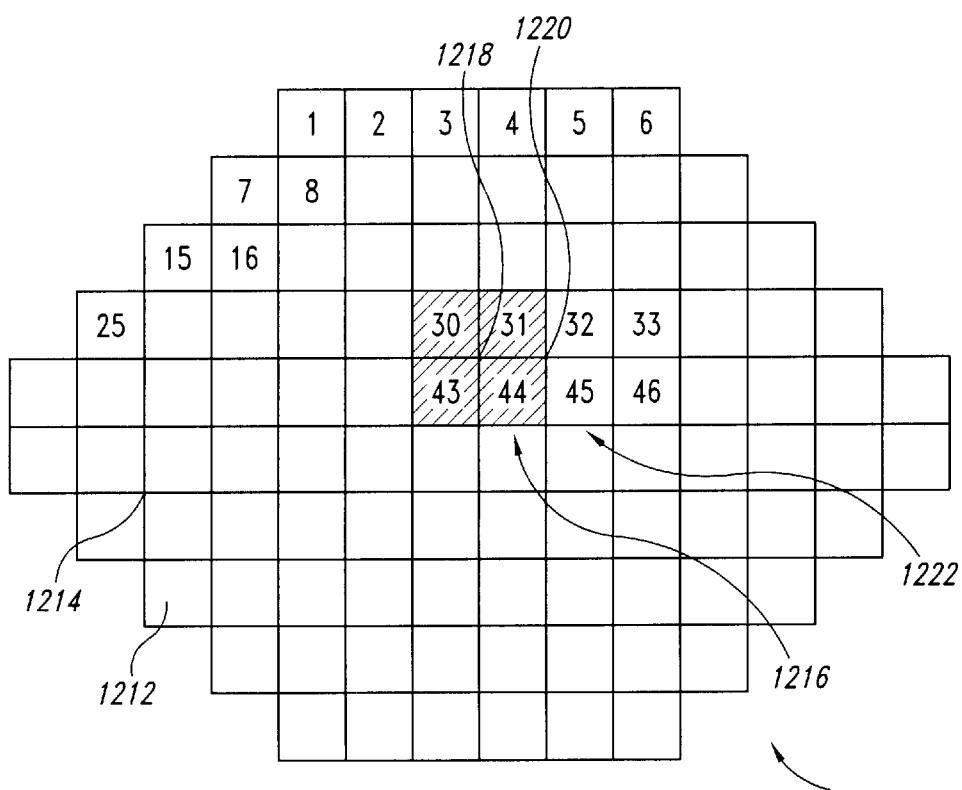
FIG. 10 is a schematic diagram of a fourth embodiment of an ultrasound probe used in the apparatus of FIG. 1.

Another embodiment of a probe 128 is illustrated in FIG. 10. This embodiment is similar to the probe illustrated in FIG. 9, except that instead of triangular transducer elements 1112 arranged in a hexagonal region 1110, the plurality of transducer elements are arranged in a polygonal region 1210, where each of the squares represents a transducer element 1212. The square elements 1212 are joined together at a plurality of points 1214. The diagnostic beam is radiated from a square region 1216, defined by the activated square elements 30–31 and 43–44, and centered about the point 1218. Like before, the diagnostic beam can then be sequentially relocated to an adjacent point 1220, such that the ultrasound beam is emitted from square elements 31–32 and 44–45 of a square region 1222, for example. The square elements 31 and 44 form the overlapping regions with the initial square region 1216.

The embodiments of the probes 128 shown in FIGS. 9 and 10 further include the capability of steering the beam emanating from a particular point 1118 or 1218 by electronically phasing the associated radiating elements. Steering the beam accommodates the fact that the blood flow and the beam center (1118 or 1218) do not necessarily lie on an axis perpendicular to the transducer face. Such a method of steering the ultrasound beam is well understood to one skilled in the art, and a more detailed explanation has been omitted in the interests of brevity.

The host computer 924 may be programmed to carry out the procedure previously described using the probe 128 illustrated in FIGS. 9 and 10. Automating the ultrasound system in such a fashion allows useful results to be obtained by those who are not trained experts in ultrasound. As mentioned previously, the host computer may be programmed with conventional pattern recognition software to interpret the resulting Doppler image of the blood flow and determine an optimal temporal window. After locating the optimal window, the host computer 924 administers pulsed ultrasound in a therapeutic mode. Although automation of the ultrasound system has been described with respect to administering diagnostic and therapeutic ultrasound in transcranial applications, it will be appreciated that a computer controlled ultrasound system may be applied to cardiac and other physiological systems as well.

The above description of illustrated embodiments of the invention is not intended to be exhaustive or to limit the invention to the precise forms disclosed. While specific embodiments of, and examples for, the invention are described herein for illustrative purposes, various equivalent modifications are possible within the scope of the invention, as those skilled in the relevant art will recognize. For instance, while specific frequencies have been identified throughout the description, embodiments of the invention can be practiced using other frequencies. Further, the various parameters that determine the effectiveness of the combined diagnostic and therapeutic ultrasound may vary from one patient to another. Therefore, it is possible that a given frequency of the therapeutic beam 222 is more effective for one patient than it is for another patient.

These and other modifications can be made in light of this detailed description. Accordingly, the invention is not limited by the disclosure, but instead the scope of the invention is to be determined entirely by the following claims, which are to be construed in accordance with established doctrines of claim interpretation.

What is claimed is:

1. A method of treating a patient suffering from thrombosis, the method comprising:

positioning a single ultrasound probe external to a body of the patient;

in a diagnostic mode, administering pulsed ultrasound from the single probe to the patient at a first frequency for a first period of time to locate a target region within the body of the patient along a diagnostic beam axis, the diagnostic beam originating from a diagnostic ultrasound source and along which the pulsed ultrasound propagates; and in a therapeutic mode, administering ultrasound from the single probe substantially along the diagnostic beam axis to the target region at a second frequency for a second period of time to enhance a thrombolytic action of a thrombolytic agent.

2. The method of claim 1, further comprising externally administering the thrombolytic agent into the patient prior to administering the ultrasound in the therapeutic mode.

3. The method of claim 1, further comprising externally administering the thrombolytic agent, the thrombolytic agent comprising tissue plasminogen activator (t-PA), recombinant t-PA (rt-PA), TNK tPA, urokinase, or streptokinase.

4. The method of claim 1 wherein the thrombolytic agent comprises a naturally occurring agent in the patient.

5. The method of claim 1 wherein the ultrasound administered in the therapeutic mode comprises pulsed or continuous-wave ultrasound.

6. The method of claim 1 wherein the first frequency is different from the second frequency.

7. The method of claim 1 wherein the first and second frequencies comprise a substantially 2 MHz frequency.

8. The method of claim 1 wherein the first frequency comprises a substantially 2 MHz frequency, and the second frequency comprises a frequency substantially between 1 MHz and 3 MHz.

9. The method of claim 1 wherein the second frequency comprises a frequency below 200 kHz.

10. The method of claim 1 wherein administering ultrasound in the diagnostic and therapeutic modes is controlled by a computer.

11. The method of claim 1 wherein administering ultrasound in the diagnostic and therapeutic modes occurs simultaneously.

12. The method of claim 1 wherein the second period of time is greater than the first period of time.

13. The method of claim 1 wherein administering ultrasound in the diagnostic and therapeutic modes comprises applying ultrasound to a cranial region of the patient.

14. The method of claim 1 wherein administering ultrasound in the diagnostic and therapeutic modes comprises applying ultrasound to a region of the leg of the patient.

15. The method of claim 1 wherein administering ultrasound in the diagnostic and therapeutic modes comprises applying ultrasound to the heart of the patient.

16. The method of claim 1 wherein administering ultrasound in the diagnostic and therapeutic modes comprises applying ultrasound to the pulmonary artery of the patient.

17. The method of claim 1 wherein the ultrasound is administered from the single probe in the diagnostic mode having a derated spatial peak temporal average intensity less than 720 mW/cm$^2$ in water.

18. The method of claim 1 where in administering ultrasound in the therapeutic mode comprises administering ultrasound having an spatial peak temporal average intensity less than 50 mW/cm$^2$ at a middle cerebral artery.

19. The method of claim 1 wherein administering ultrasound comprises intermittently transmitting a signal having a substantially sinusoidal waveform.

20. The method of claim 1 wherein ultrasound in the diagnostic and therapeutic modes is administered intermittently.

21. The method of claim 1, further comprising administering a ultrasound in the therapeutic mode with a wider beam profile than the pulsed ultrasound administered in the diagnostic mode.

22. The method of claim 1, further comprising repeating administration of the ultrasound in the diagnostic and therapeutic modes until thrombosis is substantially eliminated.

23. The method of claim 1, further comprising:
selecting a region on a body surface of the patient;
defining a plurality of areas within the region;
administering the pulsed ultrasound to a first one of the areas during the diagnostic mode and evaluating a window through that first area;
if the window through the first area is not an optimum window, administering the pulsed ultrasound to a second one of the areas in the diagnostic mode and evaluating a window through the second area, at least a portion of the second area including at least a portion of the one area; and
repeating the administering the pulsed ultrasound to another area in the diagnostic mode if prior areas administered with pulsed ultrasound do not substantially include the optimum window, until an area having substantially the optimum window is located.

24. The method of claim 23 wherein defining a plurality of areas comprises placing on the body surface an ultrasound probe having a plurality of transducer elements arranged in an array, the array defining an area corresponding to the region.

25. The method of claim 23 wherein administering ultrasound and repeating the administering are controlled by a computer.

26. The method of claim 1, further comprising:
selecting a region on a body surface of the patient;
defining a plurality of areas within the region;
administering the pulsed ultrasound to a first one of the areas during the diagnostic mode and evaluating a window through that first area;
if the window through the first area is not an optimum window, administering the pulsed ultrasound to a second one of the areas in the diagnostic mode and evaluating a window through the second area, at least a portion of the second area including at least a portion of the first area;
repeating administering the pulsed ultrasound to another area in the diagnostic mode if prior areas administered with pulsed ultrasound do not substantially include the optimum window, until an area having substantially the optimum window is located; and
administering ultrasound in the therapeutic mode through the area having substantially the optimum window.

27. The method of claim 26 wherein defining a plurality of areas comprises placing on the body surface an ultrasound probe having a plurality of transducer elements arranged in an array, the array defining an area corresponding to the region.

28. The method of claim 26 wherein administering the pulsed ultrasound in the diagnostic mode, repeating the administering, and administering ultrasound in the therapeutic mode are controlled by a computer.

29. The method of claim 1, further comprising determining blood flow at a plurality of locations along a beam axis of the pulsed ultrasound during the diagnostic mode.

30. A method of treating a patient suffering from thrombosis, the method comprising:
positioning a single ultrasound probe external to the body of the patient, the single probe having a diagnostic mode and a therapeutic mode;
in the diagnostic mode, administering a diagnostic ultrasound from the single probe to the patient at a first frequency, the diagnostic ultrasound originating from a diagnostic ultrasound beam source and directed from the diagnostic ultrasound beam source along a first beam axis; and
in the therapeutic mode, administering therapeutic ultrasound from the single probe to the patient at a second frequency to enhance a thrombolytic action of a thrombolytic agent, the therapeutic ultrasound originating from a therapeutic ultrasound beam source and directed from the therapeutic ultrasound beam source along a second beam axis, the diagnostic and therapeutic ultrasound administered from overlapping ultrasound beam sources.

31. The method of claim 30 wherein the diagnostic and therapeutic ultrasound are administered simultaneously.

32. The method of claim 30 wherein the therapeutic ultrasound is administered for a period of time greater than the diagnostic ultrasound.

33. The method of claim 30 wherein administering the diagnostic and therapeutic are intermittently repeated.

34. The method of claim 30 wherein positioning the single ultrasound probe comprises:
mounting the single ultrasound probe on to a headframe device, the headframe device having a movable mount structured to allow the single ultrasound probe to be positioned at a plurality of different orientations with respect to the body surface of the patient; and
attaching the headframe on to a cranial region of the patient.

35. The method of claim 30 wherein the single ultrasound probe comprises a first crystal superimposed over a second crystal and wherein the first frequency is administered from the first crystal in the diagnostic mode and the second frequency is administered from the second crystal in the therapeutic mode.

36. The method of claim 30 wherein the single ultrasound probe comprises an outer element annularly arranged around an inner element and wherein the second frequency is administered from the inner element in the therapeutic mode and the first frequency is administered from the inner and outer elements in the diagnostic mode.

37. The method of claim 30, further comprising providing information to a user concerning blood flow by displaying graphical information depicting blood flow at a plurality of locations along a beam axis of the pulsed ultrasound.

38. The method of claim 30, further comprising providing information to a user concerning blood flow by:
displaying first graphical information depicting blood flow at a plurality of locations along a beam axis of the pulsed ultrasound; and
displaying second graphical information depicting blood flow velocities at a selected one of the locations, the first and second graphical information being displayed simultaneously.

39. The method of claim 30, further comprising determining blood flow at a plurality of locations along a beam axis of the diagnostic ultrasound during the diagnostic mode.

40. The method of claim 30 wherein the first and second beam axes are coincident.

41. An apparatus to treat a patient suffering from thrombosis, the apparatus comprising:
a single ultrasound probe structured for positioning proximate to a region of a body of the patient to transmit pulsed ultrasound in a diagnostic mode and ultrasound in a therapeutic mode, the ultrasound having a characteristic in the therapeutic mode that is different from a characteristic of the pulsed ultrasound in the diagnostic mode, the single ultrasound probe having a diagnostic ultrasound beam source and a therapeutic ultrasound beam source from which the ultrasound in the respective modes originates, the diagnostic and therapeutic ultrasound beam sources arranged to produce an ultrasound beam in each mode that overlaps the other at the respective beam source; and
a controller structured to switch the single ultrasound probe between the diagnostic and therapeutic modes and to process ultrasound Doppler signals returned by the single ultrasound probe during the diagnostic mode.

42. The method of claim 41, further comprising a headframe device structured to be worn on the head of a patient and having a movable mount onto which the single ultrasound probe is mounted, the movable mount structured to allow the single ultrasound probe to be positioned at a plurality of different orientations with respect to the body surface of the patient.

43. The apparatus of claim 41, wherein the single ultrasound probe comprises two transducer elements.

44. The apparatus of claim 43 wherein the two transducer elements comprise a first crystal and a second crystal, respectively, the first crystal superimposed on the second crystal, and the single ultrasound probe structured to transmit a first frequency from the first crystal in the diagnostic mode and to transmit a second frequency different from the first frequency from the second crystal in the therapeutic mode.

45. The apparatus of claim 43 wherein the two transducer elements comprise an outer element and an inner element, the outer element annularly arranged over the inner element, and the single ultrasound probe structured to transmit ultrasound from the inner element in the therapeutic mode and to transmit the pulsed ultrasound from the inner and outer elements in the diagnostic mode.

46. The apparatus of claim 41 wherein the single ultrasound probe comprises plurality of transducer elements arranged in an array, the array defining an area.

47. The apparatus of claim 46 wherein each of the transducer elements is triangular shaped, and the area is hexagonal shaped.

48. The apparatus of claim 46 wherein each of the transducer elements is rectangular shaped, and the area is polygonal.

49. The apparatus of claim 46, wherein the plurality of transducer elements comprises 128 transducer elements.

50. The apparatus of claim 41, further comprising a graphical display responsive to the controller and coupled to the single ultrasound probe, the graphical display having a blood locator display structured to depict a plurality of locations along an ultrasound beam axis at which blood flow is detected, the blood locator display responsive to the controller to depict the plurality of locations during the diagnostic mode based on the Doppler signals.

51. The apparatus of claim 50 wherein the graphical display further comprises:
a location indicator to identify a selected one of the plurality of locations; and
a spectogram to depict detected blood flow velocities as a function of time at the selected location.

52. The apparatus of claim 41, wherein the controller is structured to drive the single ultrasound probe to transmit a pulsed ultrasound in both the therapeutic and diagnostic modes at a substantially 2 MHz frequency.

53. The apparatus of claim 41 wherein the controller is structured to drive the single ultrasound probe to transmit a pulsed or continuous-wave ultrasound in the therapeutic mode.

54. The apparatus of claim 41 wherein the controller is structured to drive the single ultrasound probe to transmit a pulsed or continuous-wave ultrasound in the therapeutic mode for a period of time greater than a period of time to transmit the pulsed ultrasound in the diagnostic mode.

55. The apparatus of claim 41 wherein the controller is structured to drive the single ultrasound probe to transmit ultrasound in the therapeutic and diagnostic modes simultaneously.

56. The apparatus of claim 41 wherein the single ultrasound probe is structured to transmit a pulsed or continuous-wave ultrasound in the therapeutic mode with a beam profile wider than a beam profile of the pulsed ultrasound in the diagnostic mode.

57. The apparatus of claim 41 wherein the controller processes ultrasound Doppler signals returned by the single ultrasound probe during the diagnostic mode to determine blood flow at a plurality of locations along a beam axis of the pulsed ultrasound.

58. An apparatus to treat a patient suffering from thrombosis, the apparatus comprising:
a single ultrasound probe structured to transmit pulsed ultrasound in a diagnostic mode along a diagnostic beam axis, the diagnostic beam axis originating at an ultrasound source and along which the pulsed ultrasound propagates and to transmit ultrasound in a therapeutic mode along the diagnostic beam axis, the ultrasound having a characteristic in the therapeutic mode that is different from a characteristic of the pulsed ultrasound in the diagnostic mode; and
a controller structured to switch the single ultrasound probe between the diagnostic and therapeutic modes and to process ultrasound Doppler signals returned by the single ultrasound probe during the diagnostic mode.

* * * * *

UNITED STATES PATENT AND TRADEMARK OFFICE
CERTIFICATE OF CORRECTION

PATENT NO. : 6,635,017 B1
DATED : October 21, 2003
INVENTOR(S) : Mark A. Moehring, Arne H. Voie and Merrill P. Spencer It is certified that error appears in the above-identified patent and that said Letters Patent is hereby corrected as shown below:

Title page,
Item [56], References Cited, U.S. PATENT DOCUMENTS, reads "Omitted reference" should read -- 6,102,860 A 8/2000 Mooney ...........600/443 --

Column 4,
Line 54, reads "agent may" should read -- agent may be --

Column 8,
Line 13, reads "by depth" should read -- by a depth --

Column 11,
Line 38, reads "signal processor PI" should read -- signal processor P1 --

Column 12,
Line 6, reads "such that the both the" should read -- such that both the --
Line 30, reads " the number 128," should read -- the number 128, --

Column 15,
Line 22, reads " a ultrasound" should read -- an ultrasound --

Column 16,
Line 44, reads "and therapeutic are" should read -- and therapeutic ultrasound are --

Column 17,
Line 63, reads "comprises plurality" should read -- comprises a plurality --

Signed and Sealed this

Twenty-seventh Day of July, 2004

JON W. DUDAS
*Acting Director of the United States Patent and Trademark Office*